(12) United States Patent
Furukawa et al.

(10) Patent No.: US 7,393,698 B2
(45) Date of Patent: Jul. 1, 2008

(54) MAGNETIC FINE PARTICLES AND PROCESS FOR PRODUCING THE SAME

(75) Inventors: Hirotaka Furukawa, Yokohama (JP); Noriyuki Ohnishi, Yokohama (JP); Kazunori Kataoka, Tokyo (JP); Katsuhiko Ueno, Tsukuba (JP)

(73) Assignees: National Institute of Advanced Industrial Science and Technology, Tokyo (JP); Chisso Corporation, Osaka (JP)

( * ) Notice: Subject to any disclaimer, the term of this patent is extended or adjusted under 35 U.S.C. 154(b) by 787 days.

(21) Appl. No.: 10/362,166

(22) PCT Filed: Aug. 20, 2001

(86) PCT No.: PCT/JP01/07120

§ 371 (c)(1),
(2), (4) Date: Feb. 21, 2003

(87) PCT Pub. No.: WO02/16528

PCT Pub. Date: Feb. 28, 2002

(65) Prior Publication Data
US 2003/0175826 A1    Sep. 18, 2003

(30) Foreign Application Priority Data
Aug. 21, 2000    (JP) .............................. 2000-249817

(51) Int. Cl.
*G01N 33/553* (2006.01)
*G01N 33/545* (2006.01)
*C07K 17/08* (2006.01)
*C12N 11/08* (2006.01)
*C07D 495/04* (2006.01)
*C08F 20/56* (2006.01)
*A61K 47/48* (2006.01)

(52) U.S. Cl. ..................... 436/526; 436/531; 436/532; 435/6; 435/7.5; 435/7.72; 435/188; 522/175; 530/815

(58) Field of Classification Search ................... 435/7.5, 435/969, 6, 7.72, 188; 436/518, 526, 531, 436/532; 427/488; 522/175; 530/815
See application file for complete search history.

(56) References Cited

U.S. PATENT DOCUMENTS

| 4,912,032 A | | 3/1990 | Hoffman et al. |
| 5,445,971 A | * | 8/1995 | Rohr ........................ 436/526 |
| 5,738,984 A | * | 4/1998 | Shoseyov ...................... 435/4 |
| 5,855,790 A | * | 1/1999 | Bradbury et al. ............ 210/676 |
| 6,884,628 B2 | * | 4/2005 | Hubbell et al. .............. 436/518 |

FOREIGN PATENT DOCUMENTS

WO    99/24609    5/1999

OTHER PUBLICATIONS

O'Callaghan et al. BirA Enzyme: Production and Application in the Study of Membrane Receptor-Ligand Interactions by Site-Specific Biotinylation. Analytical Biochemistry 266, 9-15 (1999).*
A. Kondo, "Development and application of thermo-sensitive magnetic immunomicrosperes for antibody purification", Applied Microbiology and Biotechnology, vol. 41, pp. 99 to 105, 1994.
A. Kondo, "Preparation of thermo-sensitive magnetic hydrogel microspheres and application to enzyme immobilization", Journal of Fermentation and Biotechnology, vol. 84, No. 4, pp. 337 to 341, 1997.
Howard Haas, "Synthetic thermally reversible gel systems", Journal of Polymer Science, Part A-1, vol. 8, No. 7, pp. 1725-1730, 1970.
Howard Haas, "Synthetic thermally reversible gel systems", Journal of Polymer Science, Part A-1, vol. 8, No. 5, pp. 1213 to 1226, 1970.

* cited by examiner

*Primary Examiner*—Long V. Le
*Assistant Examiner*—Shafiqul Haq
(74) *Attorney, Agent, or Firm*—Wenderoth, Lind & Ponack, LLP

(57) ABSTRACT

The present invention relates to magnetic fine particles having immobilized thereto a polymer having an upper critical solution temperature, and a process for producing the same, a method of separating or concentrating a microorganism, a method of purifying, detecting, or concentrating a nucleic acid, a separating agent, a method of separating a biological substance, and a method of converting a substance.

22 Claims, No Drawings

MAGNETIC FINE PARTICLES AND PROCESS FOR PRODUCING THE SAME

This application is a 371 of international application No. PCT/JP01/07120, filed Aug. 20, 2001.

TECHNICAL FIELD

The present invention relates to magnetic fine particles and a process for producing the same, a method of separating or concentrating a microorganism, a method of purifying, detecting, or concentrating a nucleic acid, a separating agent, a method of separating a biological substance, and a method of converting a substance.

BACKGROUND ART

Applied. Microbiol. Biotechnol., 1994, Vol. 41, pp. 99-105 and Journal of fermentation and Bioengineering, 1997, Vol. 84, pp. 337-341 have disclosed stimuli-responsible magnetic fine particles wherein polyisopropylacrylamide having a lower critical solution temperature (hereinafter referred to as "LCST") are immobilized to magnetic fine particles having a particle size of about 100 to 200 nm.

Since the stimuli-responsible magnetic fine particles have a small particle size of about 100 to 200 nm, the particles can be well dispersed in water. When an aqueous solution of the stimuli-responsible magnetic fine particles is heated to raise the temperature to the LCST or higher, the stimuli-responsible magnetic fine particles precipitate and aggregate. Since the aggregate can be easily recovered by magnetism, there are attempts to separate a variety of biological molecules and microorganisms using the stimuli-responsible magnetic fine particles to which an antibody or antigen is immobilized.

However, in the case of separating a biological molecule or the like by the above-mentioned method, it is necessary to raise the temperature of a solution containing the objective substance and the stimuli-responsible magnetic fine particles. Depending on the LCST of the stimuli-responsible magnetic fine particles to be used and also thermal stability of the objective substance, the biological substance or the like as the objective substance may be damaged or inactivated in some cases.

DISCLOSURE OF THE INVENTION

The present inventors have extensively studied for solving the above problems of the conventional technology. As a result, they have found that, when magnetic fine particles to which a polymer having an upper critical solution temperature is immobilized are used for separating a biological molecule or the like, it is possible to separate or recover the objective biological molecule or the like without damaging or inactivating it. Based on the findings, they have accomplished the invention.

The invention includes the following constitutions.

(1) Magnetic fine particles having immobilized thereto a polymer having an upper critical solution temperature.

(2) The magnetic fine particles according to the above (1), wherein said polymer having an upper critical solution temperature is a polymer obtained by polymerizing a monomer represented the following general formula (1):

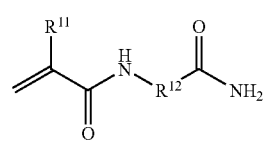

wherein $R^{11}$ represents a hydrogen atom or a methyl group and $R^{12}$ represents a single bond or a linear or branched alkylene group having 1 to 5 carbon atoms.

(3) The magnetic fine particles according to the above (1), wherein said polymer having an upper critical solution temperature is a polymer obtained by polymerizing the monomer represented by the above general formula (1) and a monomer represented the following general formula (2):

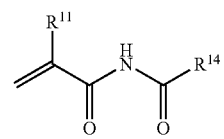

wherein $R^{13}$ represents a hydrogen atom or a methyl group and $R^{14}$ represents a hydrogen atom, a linear, branched, or cyclic alkyl group having 1 to 10 carbon atoms, an alkoxyl group, an alkylamino group, an aryl group, or a heterocyclic group.

(4) The magnetic fine particles according to the above (1), wherein said polymer having an upper critical solution temperature is a polymer obtained by polymerizing the monomer represented by the above general formula (1) and a monomer having biotin as part of its structure.

(5) The magnetic fine particles according to any one of the above (2) to (4), wherein said polymer having an upper critical solution temperature is a polymer obtained by polymerization additionally using at least one monomer selected from hydrophilic monomers and hydrophobic monomers.

(6) The magnetic fine particles according to the above (1), wherein one of one pair of substances having a mutual specific action is immobilized to said polymer having an upper critical solution temperature.

(7) The magnetic fine particles according to the above (6), wherein said one pair of substances having a mutual specific action is at least one combination selected from combinations of biotin and avidin, an antigen and an antibody, a polynucleotide and a polynucleotide having a complementary base sequence, a cDNA and an mRNA, an enzyme (active site) and a substrate, an enzyme (active site) and a product, an enzyme (active site) and a competitive inhibitor, an enzyme (coenzyme binding site) and a coenzyme, an enzyme (coenzyme binding site) and a triazine dye, a protease and a protease inhibitor, an Fc site and protein A, an Fc site and protein G, lectin and a sugar, a hormone receptor and a hormone, a DNA and a DNA binding protein, heparin and fibronectin, and heparin and laminin.

(8) The magnetic fine particles according to the above (6), wherein said one pair of substances having a mutual specific action are biotin and avidin.

(9) The magnetic fine particles according to the above (6), wherein one of said one pair of substances having a mutual specific action, immobilized to said polymer having an upper critical solution temperature is biotin.

(10) The magnetic fine particles according to the above (9), wherein said biotin is biotin bound to avidin (hereinafter referred to as "avidin-bound biotin").

(11) The magnetic fine particles according to the above (9), wherein an avidinylated enzyme is bound to said biotin.

(12) The magnetic fine particles according to the above (10), wherein a biotinylated enzyme is bound to said avidin-bound biotin.

(13) A conversion method comprising converting a substance using said magnetic fine particles according to the above (11) or (12).

(14) The magnetic fine particles according to the above (9), wherein an avidinylated antibody is bound to said biotin.

(15) The magnetic fine particles according to the above (10), wherein a biotinylated antibody is bound to said avidin-bound biotin.

(16) A separation or concentration method comprising separating or concentrating a microorganism using said magnetic fine particles according to the above (14) or (15).

(17) The magnetic fine particles according to the above (9), wherein an avidinylated molecular chaperon is bound to said biotin.

(18) The magnetic fine particles according to the above (10), wherein a biotinylated molecular chaperon is bound to said avidin-bound biotin.

(19) A modification method comprising modifying a denatured protein using said magnetic fine particles according to the above (17) or (18).

(20) The magnetic fine particles according to the above (9), wherein an avidinylated heat shock protein is bound to said biotin.

(21) The magnetic fine particles according to the above (10), wherein a biotinylated heat shock protein is bound to said avidin-bound biotin.

(22) A modification method comprising modifying a denatured protein using said magnetic fine particles according to the above (20) or (21).

(23) The magnetic fine particles according to the above (9), wherein an avidinylated nucleic acid is bound to said biotin.

(24) The magnetic fine particles according to the above (10), wherein a biotinylated nucleic acid is bound to said avidin-bound biotin.

(25) A purification, detection or concentration method comprising purifying, detecting or concentrating a nucleic acid using said magnetic fine particles according to the above (23) or (24).

(26) A method of detecting a nucleic acid comprising amplifying said nucleic acid obtained by said method of purifying or concentrating the nucleic acid according to the above (25).

(27) The method of detecting a nucleic acid according to the above (26), wherein said amplification is carried out by PCR method or RT-PCR method.

(28) A separating agent containing the magnetic fine particles according to any one of the above (1) to (10).

(29) A separation method comprising separating a biological substance using said separating agent according to the above (28).

(30) A process for producing magnetic fine particles having an upper critical solution temperature, comprising carrying out polymerization in the presence of magnetic fine particles to obtain a polymer having an upper critical solution temperature.

(31) The process for producing magnetic fine particles having an upper critical solution temperature according to the above (30), wherein a monomer represented the above general formula (1) is polymerized in the presence of magnetic fine particles.

(32) The process for producing magnetic fine particles having an upper critical solution temperature, wherein the monomer represented by the above general formula (1) and a monomer represented the general formula (2) are polymerized in the presence of magnetic fine particles.

(33) The process for producing magnetic fine particles having an upper critical solution temperature, wherein the monomer represented by the above general formula (1) and a monomer having biotin as part of its structure are polymerized in the presence of magnetic fine particles.

(34) The process for producing magnetic fine particles according to any one of the above (30) to (33), wherein at least one monomer selected from hydrophilic monomers and hydrophobic monomers is used as an additional monomer.

BEST MODE FOR CARRYING OUT THE INVENTION

The following will describe the invention in further detail.

The polymer (hereinafter referred to as "UCST polymer") having a upper critical solution temperature (hereinafter referred to as "UCST") which is essential for the invention is a polymer having a nature that the polymer dissolves in a solvent containing the polymer when the temperature of the solvent exceeds a particular temperature and the polymer precipitates and aggregates in the solvent when the temperature is not higher than the particular temperature. UCST means the particular temperature. Moreover, a phenomenon that a polymer dissolves or precipitates wherein UCST acts as a border is called a UCST characteristic.

The above-mentioned solvent is not particularly limited and specifically includes water and a liquid containing 50% by weight or more of water. Furthermore, the liquid containing 50% by weight or more of water specifically includes biological saline, a buffer solution, and the like. Moreover, the solvent may be a mixed liquid of an organic solvent such as acetone and water as far as the liquid exhibits the UCST characteristic in a polymer-containing state.

The UCST polymer for use in the invention may be any polymer as far as it has a UCST. Specifically, the UCST polymer includes a homopolymer of acryloylglycineamide, a copolymer of acryloylglycineamide and a polymerizable biotin monomer, a copolymer of acryloylglycineamide and N-formylacrylamide, a copolymer of acrylamide and N-formylacrylamide, a copolymer of acrylamide and N-acetylacrylamide, and the like.

Of these, a polymer obtained by polymerizing a monomer represented by the following general formula (1) (hereinafter referred to as "monomer (1)") and a polymer obtained by polymerizing the monomer (1) and a monomer represented the following general formula (2) (hereinafter referred to as "monomer (2)") are particularly preferably used in the invention.

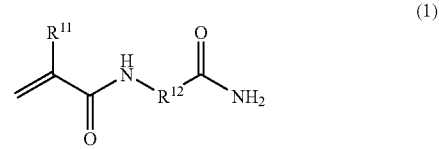

(1)

In the general formula (1), $R^{11}$ represents a hydrogen atom or a methyl group and $R^{11}$ is preferably a hydrogen atom in the invention. $R^{12}$ represents a single bond or a linear or branched alkylene group having 1 to 5 carbon atoms and $R^{12}$ is preferably a methylene group in the invention.

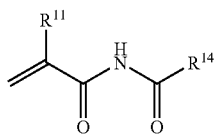

(2)

In the general formula (2), $R^{13}$ represents a hydrogen atom or a methyl group and $R^{13}$ is preferably a hydrogen atom in the invention. $R^{14}$ represents a hydrogen atom, a linear, branched, or cyclic alkyl group having 1 to 10 carbon atoms, an alkoxyl group, an alkylamino group, an aryl group, or a heterocyclic group. The alkyl group is preferably a linear alkyl group having 1 to 5 carbon atoms, and the alkyl moiety of the alkoxyl group or alkylamino group is preferably a linear alkyl group having 1 to 5 carbon atoms. The aryl group includes phenyl group, naphthyl group, and the like, and compound forming the heterocyclic group includes pyrimidine and the like.

In the polymerization for obtaining the UCST polymer, when at least one monomer selected from hydrophilic monomers and hydrophobic polymers in addition to the monomers (1) and (2), the UCST can be controlled by changing the kind and ratio thereof.

The monomer to be used is classified into a hydrophilic one or a hydrophobic one on the basis of the hydrophilicity of the monomer (1) to be used in the polymerization. That is, the one more hydrophilic than the monomer (1) to be used in the polymerization is a hydrophilic monomer and the one more hydrophobic is a hydrophobic monomer. Moreover, when two or more monomers as the monomer (1) are used in the polymerization, the classification may be carried out on the basis of the most hydrophilic monomer of them.

The hydrophilic monomer for use in the invention may vary depending on the kind of the monomer (1) to be used in the polymerization and hence is difficult to specify sweepingly, but specific examples thereof include (meth)acrylamide, (meth)acrylic acid, allyl alcohol, allylamine, and the like, and the examples of the hydrophobic monomer include alkyl (meth)acrylates, unsaturated hydrocarbons such as styrene, ethylene, propylene, and acetylene, alkyl vinyl ethers, alkyl(meth)acrylamides, and the like.

In the case that a hydrophilic monomer is used in the polymerization for obtaining the UCST polymer, the UCST tends to lower. Contrary, in the case that a hydrophobic monomer is used, the UCST tends to rise.

At the polymerization for obtaining the UCST polymer of the invention, the composition ratio of the individual monomers is not particularly limited, but the molar ratio of the monomer (1)/the monomer (2)/the other monomer is usually a ratio of 95 to 20/1 to 60/0 to 40, preferably a ratio of 95 to 50/1 to 50/0 to 20.

The raw material for the magnetic fine particles for use in the invention may be an organic or inorganic substance as far as it exhibits magnetism. In the invention, it is not limited to the following, but specifically, it includes nickel oxide particles, ferrite particles, magnetite particles, cobalt iron oxide, barium ferrite, carbon steel, tungsten steel, KS steel, rare-earth cobalt magnet fine particles, hematite particles, and the like.

The particle size of the magnetic fine particles may be such a size that the magnetic fine particles are not adsorbed by a magnetic force when the magnetic force is applied to the solvent in which the magnetic fine particles are dispersed. In the invention, the size is not particularly limited but is preferably in the range of 1 nm to 1 μm, more preferably in the range of 1 nm to 100 nm.

The process for preparing the magnetic fine particles for use in the invention is described with reference to the case of using magnetite. Magnetic magnetite fine particles having a particle size of several dozen nm can be obtained by converting magnetite into double micelles using sodium oleate and sodium dodecylbenzenesulfonate and dispersing the micelles into an aqueous solution. This process is described in Biocatalysis, 1991, Vol. 5, pp. 61-69.

The magnetic fine particles of the invention are particles to which a UCST polymer is immobilized. Also, since they are fine particles, the magnetic fine particles themselves have a UCST.

The UCST of the magnetic fine particles and UCST polymer is specifically a temperature at the time when the transmittance of visible light of magnetic fine particles- or UCST polymer-containing water, wherein the magnetic fine particles or UCST polymer is added to water in the rate of 1% by weight, reaches a half value of the value in a clear state, in the case that the magnetic fine particles- or UCST polymer-containing water is heated to be in a clear state and then the temperature of the magnetic fine particles- or UCST polymer-containing water is lowered in the rate of 1° C. per 1 minute.

There is a case that the transmittance of visible light of the magnetic fine particles- or UCST polymer-containing water reaches a half value of the value in the clear state and the half value is still maintained in a certain temperature range even when the temperature is raised or lowered. The upper limit of the temperature range is called a UCST at temperature elevation and the lower limit is called a UCST at temperature lowering. The difference of the both temperatures (temperature range) is called a switching range. With regard to the switching range, the narrower, the better and the range is preferably 10° C. or less, more preferably 0° C. in the invention.

The UCST of the magnetic fine particles of the invention is not particularly limited but is preferably in the range of 0 to 50° C., particularly preferably in the range of 0 to 40° C. in the case that the magnetic fine particles of the invention is used as a separating agent.

In the invention, a UCST polymer may be immobilized to the surface of magnetic fine particles by any action. That is, the action may be physical absorption or a chemical bond such as a hydrogen bond or a covalent bond. Specifically, as methods for the immobilization include a method of polymerizing the UCST polymer in the presence of magnetic fine particles, a method of bringing the UCST polymer into contact with magnetic fine particles in a solvent, a method of binding a coupling agent having a functional group such as SH group to magnetic fine particles and subjecting the UCST polymer to graft polymerization using the functional group as a starting point.

Of these, magnetic fine particles of the invention obtainable by the method of polymerizing the UCST polymer in the presence of magnetic fine particles are preferable because the immobilized UCST polymer is hardly eliminated from the magnetic fine particles even when dissolution and precipitation/aggregation are repeatedly carried out in a liquid containing the same.

Furthermore, a method of polymerizing only the monomer (1) or the monomer (1) and the monomer (2) in the presence of magnetic fine particles may be preferably used in the invention, and a method of polymerizing one or more monomers selected from hydrophilic monomers and hydrophobic monomers, the monomer (1) and the monomer (2) in the presence of magnetic fine particles may be particularly preferably used in the invention.

Specifically, magnetic fine particles to which a polymer is physically adsorbed can be prepared by adding the individual monomers to a solution in which magnetic fine particles are suspended, adding a polymerization initiator (e.g., ammonium persulfate or potassium persulfate) or a polymerization accelerator (e.g., N,N,N',N'-tetramethylethylenediamine) under stirring under a nitrogen atmosphere, and then stirring the mixture for several hours.

The UCST of the magnetic fine particles of the invention is preferably the same temperature as the UCST inherent in the UCST polymer. The magnetic fine particles of the invention are preferably the particles in which the immobilized UCST polymer is tightly supported even when dissolution and precipitation/aggregation are repeatedly carried out in a solution thereof.

The magnetic fine particles of the invention which have a USCT and aggregate in a liquid can be easily recovered by a magnetism, and hence can be extremely effectively used for separation, recovery, and concentration of an objective substance in a solution.

The one pair of substances having a mutual specific action is substances which mutually adsorb specifically through an interaction such as an interaction between ions, a hydrogen bond, a hydrophobic interaction, and coordination to a metal atom. Specifically, there may be mentioned combinations of biotin and avidin, an antigen and an antibody, a polynucleotide and a polynucleotide having a complementary base sequence, a cDNA and an mRNA, an enzyme (active site) and a substrate, an enzyme (active site) and a product, an enzyme (active site) and a competitive inhibitor, an enzyme (coenzyme binding site) and a coenzyme, an enzyme (coenzyme binding site) and a triazine dye, a protease and a protease inhibitor, an Fc site and protein A, an Fc site and protein G, lectin and a sugar, a hormone receptor and a hormone, a DNA and a DNA binding protein, heparin and fibronectin, and heparin and laminin, polythimine and mRNA, an antibody of *Escherichia coli* and *Escherichia coli*, and an antibody (IgG) and anti-IgG.

Of these, a combination of biotin and avidin can be most preferably used. When biotin is immobilized to the UCST polymer, it is possible to separate or recover selectively only an objective substance to which avidin is immobilized. In the case that avidin is immobilized to the UCST polymer, it is possible to separate or recover selectively only an objective substance to which biotin is immobilized.

In this connection, in the invention, biotin may be iminobiotin, and avidin may be streptoavidin. The effects of the invention can be obtained in any cases.

The objective substance at that time is not particularly limited but examples thereof include enzymes, antibodies, nucleic acids, molecular chaperons, and heat shock proteins.

In the case that avidin is immobilized to the UCST polymer, a more efficient separation or recovery of a biotinylated objective substance is enabled because it is possible to maintain the state that a maximum of three sites of four biotin-binding sites of avidin are opened.

However, since it is actually difficult to immobilize avidin directly to the UCST polymer, it is preferable to immobilize avidin to the UCST polymer through biotin for relatively easy immobilization of avidin to the UCST polymer. That is, avidin is preferably immobilized to the UCST polymer in the form of avidin-bound biotin.

When the magnetic fine particles of the invention wherein one of the one pair of substances having a mutual specific action is immobilized to the UCST polymer are used, another substance or a substance to which the substance is immobilized can be easily separated or recovered.

For example, when magnetic fine particles wherein an enzyme is immobilized to the UCST polymer are used in an enzymatic reaction, it is possible to convert a substrate at a faster rate as compared with the rate in an enzymatic reaction using a conventional immobilized enzyme. At that time, the enzyme to be used is not particularly limited but it includes oxidoreductases, transferases, hydrolases, lyases, isomerases, ligases, and the like.

The substance produced by converting a substrate can be easily separated from the enzyme by raising the temperature of the solution containing the magnetic fine particles of the invention and the produced substance to precipitate only the magnetic fine particles and removing only the thus precipitated magnetic fine particles using magnetism.

When magnetic fine particles wherein an antibody is immobilized to the UCST polymer are used, it is possible to separate or concentrate efficiently a microorganism in a solution. The antibody to be used at that time may be a monoclonal antibody or a polyclonal antibody.

The method of separating or concentrating a microorganism in a solution is not particularly limited but there may be specifically mentioned a method of adding the magnetic fine particles to a solution containing a microorganism, bringing the microorganism thoroughly into contact with the magnetic fine particles, then lowering the temperature of the solution to precipitate only the magnetic fine particles which have adsorbed the microorganism, and removing only the thus precipitated magnetic fine particles using magnetic force. By this method, it is possible to separate or concentrate a microorganism in a solution easily.

For example, when the antibody to be used is a salmonella antibody, since only salmonella in a food suspension can be easily separate or concentrate, it is possible to prepare a microorganism-assaying kit or a diagnostic agent exhibiting a high sensitivity by combining the magnetic fine particles of the invention to which any antibody is immobilized and an appropriate detecting reagent.

Since the magnetic fine particles wherein a molecular chaperon or heat shock protein is immobilized to the UCST polymer enhance stability of an enzyme or antibody in a solution, repeated use thereof becomes possible, and hence production of proteins or substances at an industrial level can be assisted. Generally, since a protein such as a molecular chaperon is expensive, it is difficult to use it at an industrial level.

There may be mentioned a method of adding the magnetic fine particles wherein a base is immobilized to the UCST polymer to a solution containing a nucleic acid and bringing the magnetic fine particles thoroughly into contact with the nucleic acid, then raising the temperature of the solution to precipitate only the magnetic fine particles which have adsorbed the nucleic acid and removing only the thus precipitated magnetic fine particles using magnetism. By this method, it is possible to separate or concentrate a nucleic acid in a solution easily. Moreover, the method of separating or concentrating a nucleic acid is applicable to purification, concentration, detection, or the like of a specific gene.

Moreover, purification, detection, or concentration of any nucleic acid can be easily carried out by effecting thoroughly hybridization in a mixed liquid containing two or more kinds of nucleic acids and the magnetic fine particles, then lowering the temperature of the mixed liquid to aggregate and recover the particles together with the nucleic acids, and again raising the temperature.

For example, target DNA or mRNA can be concentrated or purified by using a biotinylated DNA or biotinylated polythymine. A nucleic acid can be detected in a good sensitivity by amplifying the resulting nucleic acid according to any of various gene-amplifying methods. The method of amplifying a nucleic acid is not particularly limited but PCR method or RT-PCR method may be preferably used in the invention.

The method for immobilizing one of the one pair of substances having a mutual specific action to a UCST polymer immobilized to the magnetic fine particles of the invention is not particularly limited and includes a method of immobilizing one of the one pair of substances to a UCST polymer already synthesized (hereinafter referred to as "immobilization method") or a method of introducing one of the one pair of substances by polymerizing a monomer having one of the one pair of substances as part of the structure and a monomer forming a UCST polymer through polymerization (hereinafter referred to as "polymerization method").

The above-mentioned immobilization method preferably uses a covalent bond, but binding utilizing an ion-complex or a charge-transfer complex, binding utilizing a biochemical affinity, or the like may be used.

In the case that a protein such as an antibody or enzyme is bound to the UCST polymer, the UCST polymer may be bound to the protein utilizing the reactivity of a functional group such as an amino group or carboxyl group which the protein has.

For example, in the case of utilizing the amino group of a protein, an amide bond can be formed according to the reaction scheme as shown below by introducing a carboxyl group in the UCST polymer.

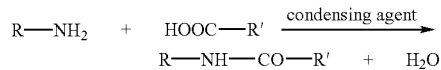

R: a protein, R': a UCST polymer

Moreover, the UCST polymer may be bound to a protein utilizing a method of using an aldehyde group or utilizing an epoxy group as shown below.

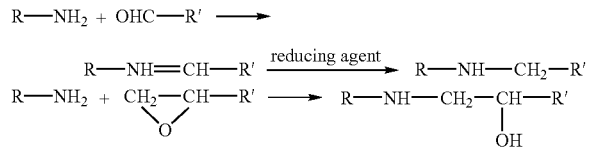

Moreover, in the case of utilizing the carboxyl group of a protein, an amide bond can be formed according to the reaction scheme as shown below by introducing an amino group in the UCST polymer.

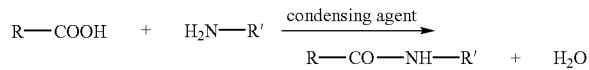

Furthermore, a protein such as an enzyme or antibody can be also immobilized to the UCST polymer according to a known protein immobilizing method using a carbodiimide or the like by designing the UCST polymer so as to have an appropriate functional group such as carboxyl group or the like, for example, through copolymerization of the carboxyl group or the like of methacrylic acid with the above monomer or the other monomer.

In the case that an antibody is introduced into the UCST polymer and then bound to a protein, the binding is preferably effected in a phosphate or Tris buffer solution whose pH is around neutral. Moreover, the salt concentration may be suitably determined depending on the purposes.

On the other hand, the polymerization method is preferably employed in the invention because it is relatively easy to control polymerization ratio in a polymer.

The method for immobilizing one of the one pair of substances having a mutual specific action to the UCST polymer immobilized to magnetic fine particles of the invention is described in detail by way of illustration of the polymerization method using a monomer having biotin as part of the structure.

The monomer forming the UCST polymer through polymerization includes N-acryloylglycineamide, N-formylacrylamide, N-acetylacrylamide, acrylamide, polymerizable biotin derivatives, and the like, while the monomer having biotin as part of the structure includes (meth)acrylamide, (meth)acrylate derivatives, and the like formed by utilizing a terminal carboxyl group of biotin, but they are not limited thereto in the invention.

The monomer forming the UCST polymer to be preferably used in the polymerization method includes the above-mentioned monomer (1), and the monomer having biotin as part of the structure includes a polymerizable biotin derivative represented by the following general formula (3).

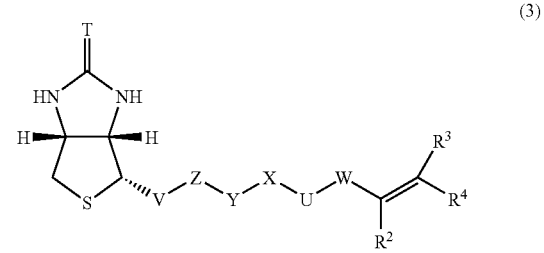

(3)

In the general formula (3), $R^2$ represents a hydrogen atom or an alkyl group. $R^3$ and $R^4$ each independently represents a hydrogen atom, an alkyl group or an aryl group. T represents an oxygen atom or =NH group. W represents a single bond or a carbonyl group, a thiocarbonyl group, or an alkylene group having 1 to 5 carbon atoms. U represents a single bond or —NH— group. X represents a single bond or a hydrocarbon bond having 1 to 8 carbon atoms, an oxygen atom, or —NH— group. Y represents a single bond or a carbonyl group, a thiocarbonyl group, —NH— group, a 1,2-dioxyethylene group, or a 1,2-diaminoethylene group. Z represents a single bond or a carbonyl group, a thiocarbonyl group, an alkylene group having 1 to 5 carbon atoms, an oxygen atom, or —NH— group. V represents a single bond or an alkylene group having 1 to 5 carbon atoms.

Furthermore, as the monomer (1), acryloylglycineamide represented by the following general formula (4) may be specifically mentioned.

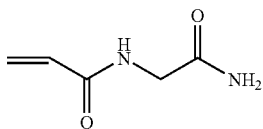
(4)

Of the monomers represented by the following general formula (3), polymerizable biotin derivatives represented by the following general formulae (5) to (7) may be preferably used in the polymerization method.

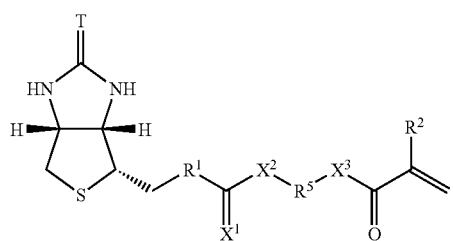
(5)

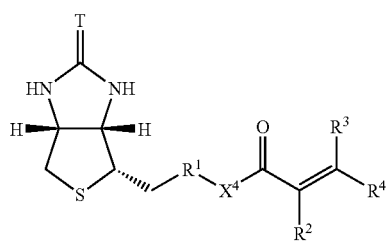
(6)

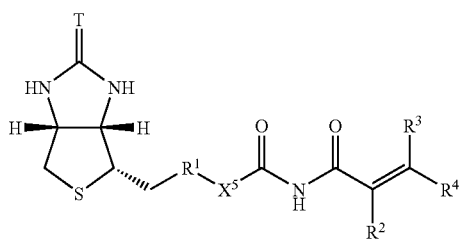
(7)

In the general formulae (5) to (7), $R^1$ represents a single bond or an alkylene group having 1 to 4 carbon atoms and $R^5$ represents an alkylene group having 2 or 3 carbon atoms. $X^1$ represents an oxygen atom or a sulfur atom, $X^2$ to $X^5$ each independently represents an oxygen atom or —NH— group. T, $R^2$, $R^3$, and $R^4$ each has the same definition as in the above general formula (3).

The polymerizable biotin derivative represented by the above general formula (5) can be generally obtained by converting the side chain carboxyl hydroxyl group of biotin or that of a biotin derivative represented by the following general formula (8) into an appropriate leaving group and then condensing the product with an acrylic derivative represented by the following general formula (9).

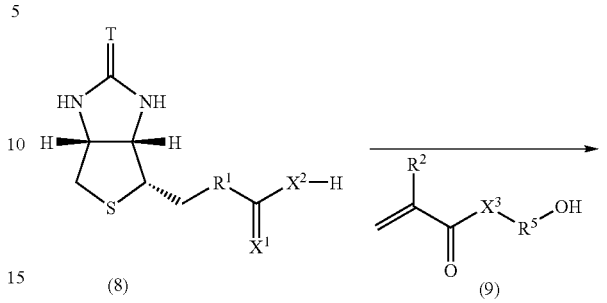

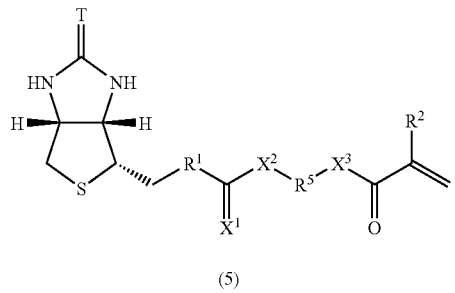
(5)

The polymerizable biotin derivative represented by the above general formula (6) can be obtained by reacting a biotin derivative represented by the following general formula (10) with an appropriate acrylating agent (including a methacrylating agent or the like; for example, an acrylating agent such as acrylic acid, acryloyl chloride, acrylic anhydride, or acryloxysuccinimide, a methacrylating agent such as methacrylic acid, methacryloyl chloride, methacrylic anhydride, or methacryloxysuccinimide, or the like).

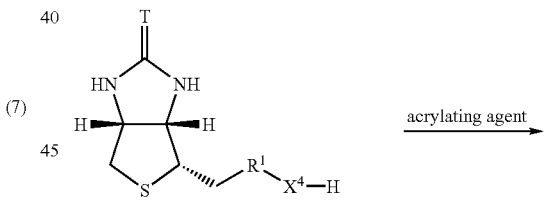

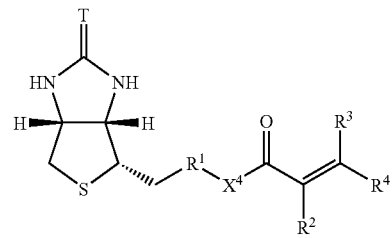
(6)

Herein, the biotin derivative represented by the above general formula (10) can be obtained by converting the hydroxyl group of an alcohol compound ($X^4$=an oxygen atom) obtainable by reducing biotin or the biotin derivative represented by the general formula (8) with an appropriate reducing agent into a functional group having a function as a leaving group and then subjecting the alcohol compound after the conversion to a substitution reaction with an amine derivative ($X^4$=—NH—).

The polymerizable biotin derivative represented by the above general formula (7) can be obtained by reacting a biotin derivative represented by the following general formula (11) with an isocyanate substance represented by the general formula (12) in an aprotic solvent such as tetrahydrofuran (THF), dimethyl sulfoxide (DMSO), ether, dimethylformamide (DMF), dichloromethane, chloroform, ethyl acetate, acetone, an aliphatic hydrocarbon, benzene, or toluene.

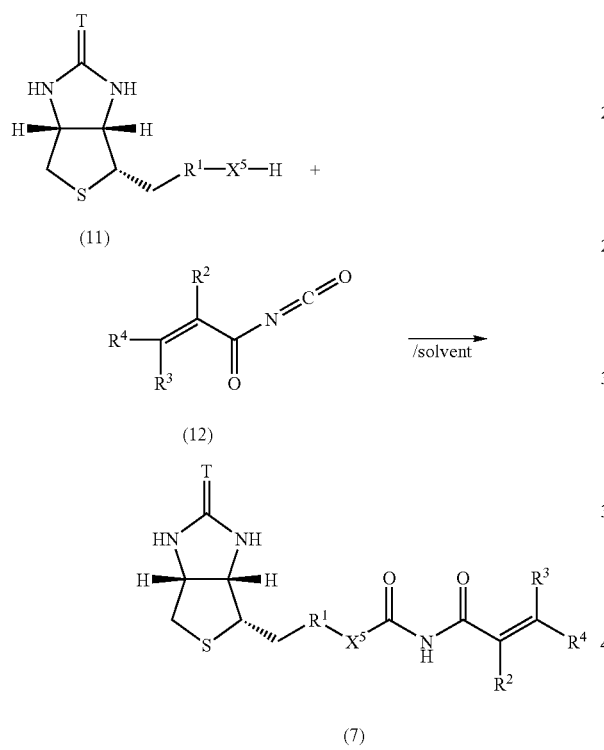

Furthermore, a polymerizable biotin derivative represented by the following general formula (13) is particularly preferably used in the polymerization method.

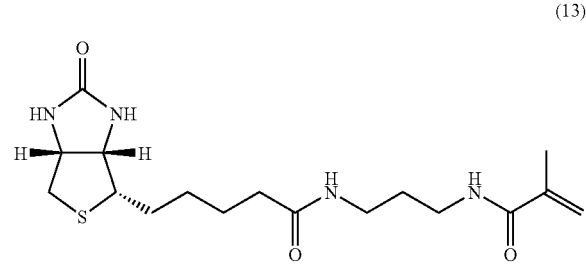

Moreover, the monomer capable of being preferably used in the polymerization method includes a biotin methacrylamide derivative represented by the general formula (14) and a biotin derivative represented by the general formula (15).

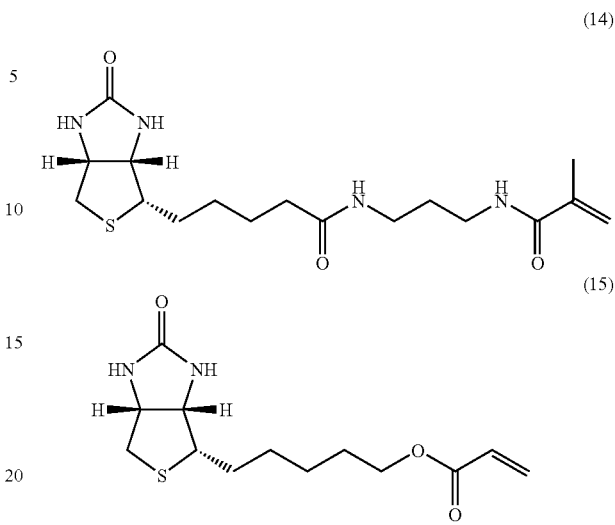

In the case that the magnetic fine particles of the invention are produced by the method of carrying out the polymerization for obtaining a UCST polymer in the presence of magnetic fine particles, contaminants such as unreacted monomers and salts coexist in the reaction solution. The contaminants may be removed by dialysis or by lowering the temperature of the solution to the UCST or lower to cause aggregation, recovering aggregated matter with a magnet, and subsequently removing the resulting supernatant.

In the immobilization of one of the one pair of substances having a mutual specific action, as mentioned above, one of the one pair of substances having a mutual specific action may be directly immobilized to the UCST polymer but, since the operations for the immobilization are simple and convenient, it is preferable to immobilize it to the UCST polymer through a binding of biotin to avidin. For example, an enzyme to which avidin is immobilized may be immobilized to the UCST polymer to which biotin is immobilized utilizing a specific adsorption action between avidin and biotin.

More preferably, for example, an enzyme to which biotin is immobilized is immobilized to the UCST polymer to which avidin-bound biotin is immobilized. As mentioned above, since the avidin-bound biotin is capable of immobilizing a maximum of three biotinylated enzymes, it is possible to convert, separate, or recover a substrate in a high efficiency. As a matter of course, it is not limited to an enzyme and any one pair of substances having a mutual specific action may result in the same effects.

The separating agent of the invention is not particularly limited as far as it contains the UCST magnetic fine particles of the invention, but the content of the magnetic fine particles in the separating agent is preferably in the range of 1 to 100% by weight, particularly preferably in the range of 2 to 30% by weight.

The other components include ferrite particles, magnetite particles, hematite particles, and the like.

The use of the separating agent of the invention enables a facile separation of a microorganism, a nucleic acid, a protein, an antigen, an endocrine-disrupting chemical, or the like.

EXAMPLES

The present invention will be illustrated in greater detail with reference to the following Examples, but the invention should not be construed as being limited thereto.

Example 1

Preparation of Magnetic Fine Particles

Magnetic fine particles are prepared according to the following method.

In a 1 L flask, 83.4 g of ferrous sulfate (heptahydrate) and 10.4 g of sodium nitrite were thoroughly mixed with 500 ml of distilled water, followed by 20 minutes of stirring at 40° C. Thereafter, 125 ml of concentrated ammonia was added thereto and insoluble matter was collected and washed twice with distilled water to obtain magnetite. The resulting magnetite was added to 500 ml of distilled water in a 1 L flask and the temperature of the solution was raised to 80° C. Then, 7.5 g of sodium oleate was added thereto, followed by 20 minutes of stirring at the same temperature. Thereafter, pH of the solution was adjusted to 5.5 and the resulting insoluble matter was collected by filtration and washed twice with distilled water to obtain magnetite having an oleic acid layer. The magnetite was again added into a 1 L flask, 500 ml of distilled water was added, and the temperature of the solution was raised to 70° C. Then, 7.5 g of sodium dodecylbenzenesulfonate was added thereto and the whole was stirred overnight to obtain magnetic fine particles. Using the magnetic fine particles, the magnetic fine particles of the invention to which a UCST polymer was immobilized were prepared according to the following method.

Example 2

Preparation of Magnetic Fine Particles to which UCST Polymer is Immobilized (Hereinafter Referred to as "UCST Magnetic Fine Particles")

Into a 300 ml flask were added 4 ml of the magnetic fine particles prepared in Example 1, 2.13 g of N-acryloylglycineamide, 12.7 mg of N-biotinyl-N'-methacryloyltrimethyleneamide, and 94 ml of distilled water, followed by thorough stirring at 50° C. Thereto was added 0.1 g of potassium persulfate, followed by 6 hours of stirring at room temperature. The resulting black clear solution was dialyzed for one day and night to obtain UCST magnetic fine particles. The UCST of the resulting black clear solution was measured to be 18° C. The UCST hardly changed in a physiological saline and in 100 mM phosphate buffer (pH 7.0).

Example 3

Separation of Avidin from Aqueous Solution

In a test tube, 50 μl of the UCST magnetic fine particles obtained in Example 2, 50 μl of 1.0% avidin solution, 100 μl of 1.0 M sodium phosphate buffer (pH 7.0), and 800 μl of distilled water were thoroughly mixed and then the temperature of the solution was lowered to the UCST or lower. The aggregate of the UCST magnetic fine particles was recovered with neodi-magnet (0.43 T), and 100 μl of the supernatant was taken out and subjected to denaturation treatment with SDS. Then, disappearance of the band corresponding to avidin in the supernatant was confirmed by SDS-polyacrylamide gel electrophoresis (SDS-PAGE).

Example 4

Specific Separation of Avidin from Albumen

In a test, 50 μl of the UCST magnetic fine particles obtained in Example 2, 50 μl of 1.0% avidin solution, 100 μl of 1.0 M sodium phosphate buffer (pH 7.0), 450 μl of distilled water, and 400 μl of 2.5% albumen solution were thoroughly mixed and then the temperature of the solution was lowered to the UCST or lower by placing the solution in ice-water. The aggregate was recovered with neodi-magnet, and 100 μl of the supernatant was taken out and subjected to denaturation treatment with SDS. Then, disappearance of only the band corresponding to avidin in the supernatant was confirmed by SDS-PAGE.

Example 5

Immobilization of Avidinylated Enzyme to UCST Magnetic Fine Particles

One hundred μl of the solution of the UCST magnetic fine particles obtained in Example 2, 1000 μl of a commercially available avidinylated peroxidase solution (1 mg/ml), 100 μl of 1.0 M sodium phosphate buffer (pH 7.0), and 700 μl of distilled water were added and thoroughly mixed. The resulting solution was cooled and the aggregate of the UCST magnetic fine particles was recovered with a magnet. After 1900 μl of the supernatant was removed, 1900 μl of 0.1 M phosphate buffer (pH 7.0) was newly added to prepare a solution of the UCST magnetic fine particles to which avidinylated peroxidase was immobilized. The solution dissolved at the UCST or higher and aggregated at the UCST or lower. The temperature of the solution was changed by means of a constant temperature bath, and operations of dissolution, aggregation, and recovery with a magnet were carried out. The activity of the peroxidase in each supernatant was measured according to the method of measuring the activity of peroxidase shown in the following. In this connection, after the recovery of the UCST magnetic fine particles with a magnet, 1900 μl of the supernatant was removed and 1900 l of 0.1 M phosphate buffer (pH 7.0) was newly added each time.

(Method of Measuring Peroxidase Activity)

In a cell of an absorptiometer, 100 μl of 100 mM hydrogen peroxide, 100 μl of 50 mM phenol, 100 μl of 50 mM 4-aminoantipyrine, 100 μl of 1.0 M sodium phosphate buffer (pH 7.0), and 580 μl of distilled water were mixed beforehand, and 20 μl of a sample taken out of the above prepared solution was added thereto. After the mixture was again thoroughly mixed, the product was measured by an increase of the absorption at 500 nm. In this connection, the above operations were carried out at 30° C.

The following shows the results of measuring enzymatic activity of the supernatant in the case that aggregation and dissolution of the UCST fine particles of the invention were repeatedly carried out according to the above method. In this connection, the enzymatic was represented by specific activity wherein the at the first dissolution was regarded as 100.

TABLE 1

| Number of repetition (time) | Peroxidase activity at dissolution of UCST magnetic fine particles (%) | Peroxidase activity of supernatant after aggregation and recovery of UCST magnetic fine particles (%) |
| --- | --- | --- |
| 1 | 100 | 13 |
| 2 | 102 | 9 |

TABLE 1-continued

| Number of repetition (time) | Peroxidase activity at dissolution of UCST magnetic fine particles (%) | Peroxidase activity of supernatant after aggregation and recovery of UCST magnetic fine particles (%) |
|---|---|---|
| 3 | 101 | 5 |
| 5 | 97 | 4 |
| 10 | 98 | 2 |
| 20 | 86 | 0 |

From these results, it was revealed that the peroxidase activity of the avidinylated peroxidase immobilized to the UCST magnetic fine particles did not disappear even when the peroxidase was subjected to repeated dissolution and aggregation together with the UCST magnetic fine particles and repetition of the operations.

Example 6

Immobilization of Biotinylated Enzyme to Avidinylated UCST Magnetic Fine Particles In order to obtain avidinylated UCST magnetic fine particles wherein three sites of biotin-binding sites of avidin were free, 50 μl of the UCST magnetic fine particles obtained in Example 2 was thoroughly mixed with 100 μl of 1.0% avidin solution, 100 μl of 1.0 M sodium phosphate buffer (pH 7.0), and 350 μl of distilled water in a test and then the temperature of the solution was lowered to the UCST or lower by placing the solution in ice-water. The aggregate was recovered with neodi-magnet (0.43 T) to obtain avidinylated UCST magnetic fine particles wherein the biotin-binding sites other than the binding site to the polymer were free.

One hundred μl of the solution of the magnetic fine particles, 1000 μl of a commercially available biotinylated peroxidase solution (1 mg/ml), 100 μl of 1.0 M sodium phosphate buffer (pH 7.0), and 700 μl of distilled water were added and thoroughly mixed. The resulting solution was cooled and the aggregate was recovered with a magnet. After 1900 μl of the supernatant was removed, 1900 μl of 0.1 M phosphate buffer (pH 7.0) was newly added to prepare avidinylated magnetic fine particles to which biotinylated peroxidase was immobilized. The following shows the results of measuring enzymatic activity of the supernatant in the case that dissolution, aggregation, and recovery were repeatedly carried out in a similar manner to Example 5 using the UCST magnetic fine particles. The enzymatic activity was also represented by specific activity wherein the activity at the first dissolution was regarded as 100.

TABLE 2

| Number of repetition (time) | Peroxidase activity at dissolution of UCST magnetic fine particles (%) | Peroxidase activity of supernatant after aggregation and recovery of UCST magnetic fine particles (%) |
|---|---|---|
| 1 | 100 | 2 |
| 2 | 99 | 1 |
| 3 | 102 | 1 |
| 5 | 98 | 0 |
| 10 | 96 | 0 |
| 20 | 90 | 0 |

From these results, it was revealed that the peroxidase activity of the biotinylated peroxidase bound to the UCST magnetic fine particles to which avidin was immobilized did not disappear even when the peroxidase was subjected to repeated dissolution and aggregation together with the UCST magnetic fine particles and repetition of the operations.

Example 7

Immobilization of Molecular Chaperon to UCST Magnetic Fine Particles

A commercially available biotinylated heat shock protein HSP70 was thoroughly mixed with 100 mM sodium phosphate buffer (pH 7.0) and the 5 μl of the mixture was taken out. After denaturation treatment, the band of HSP70 was confirmed by SDS-PAGE. Subsequently, 50 μl of the avidinylated UCST magnetic fine particles wherein the biotin-binding sites other than the binding site to the polymer were free prepared in Example 6 was added to 50 μl of the above sodium phosphate buffer solution of the biotinylated HSP70 and the whole was thoroughly mixed. Thereafter, as in Example 3, the solution was cooled to aggregate the magnetic fine particles, which was recovered with a magnet. HSP70 in the supernatant was similarly investigated by SDS-PAGE to confirm that HSP70 was absent in the supernatant and was bound to avidin immobilized to the magnetic fine particles.

Example 8

Method of Separating and Concentrating Microorganism

A commercially available biotinylated salmonella antibody was immobilized to the avidinylated UCST magnetic fine particles, prepared in Example 6, wherein the biotin-binding sites other than the binding site to the polymer were free. The immobilization was confirmed using SDS-PAGE. Subsequently, 1 ml of the solution of the biotinylated salmonella antibody-immobilized UCST magnetic fine particles was added to 20 ml of a bacteria suspension which was adjusted so as to contain the salmonella in a rate of one bacteria/ml and the whole was thoroughly mixed. Thereafter, as in Example 3, the solution was cooled to aggregate the magnetic fine particles, which was recovered with a magnet. The supernatant was removed and a 1 ml solution was prepared. The solution was sterilized beforehand and added to 20 ml of a brain-heart infusion agar medium and the whole was rapidly mixed. Then, the mixture was spread in a petri dish and allowed to stand to cool until the agar became hard, followed by 48 hours of incubation at 37° C. The following shows the results of measuring the number of colonies after 48 hours. These all the operations were carried out in a clean workstation. Additionally, the number of bacteria in 1 ml of the bacteria suspension originally prepared was similarly measured as a control without adding the magnetic fine particles.

TABLE 3

|  | Control | Use of UCST magnetic fine particles |
|---|---|---|
| Number of colonies | 1 | 19 |

From the results, it was apparent that salmonella was concentrated by the magnetic fine particles

Example 9

Immobilization of Nucleic Acid to UCST Magnetic Fine Particles

To 500 µl of a commercially available biotinylated labeled DNA fragment (50 to 1000 bp) were added 450 µl of distilled water and 50 µl of avidinylated UCST magnetic fine particles, prepared in Example 6, wherein the biotin-binding sites other than the binding site to the polymer were free, and the whole was thoroughly mixed. Thereafter, as in Example 3, the solution was cooled to aggregate the UCST magnetic fine particles, which was recovered with a magnet. The confirmation of the DNA fragment in the supernatant by agarose gel electrophoresis suggested that all the DNA fragments were bound to the UCST magnetic fine particles. Through a similar experiment on RNA, the binding to the UCST magnetic fine particles was confirmed.

Example 10

UCST magnetic fine particles were prepared in accordance with Example 2 with the exception that 252 mg of methacrylamide was used instead of N-biotinyl-N'-methacryloyltrimethyleneamide. The UCST of the resulting magnetic fine particles was found to be 2° C.

Example 11

UCST magnetic fine particles were prepared in accordance with Example 2 with the exception that 251 mg of N-acetylacrylamide was used instead of N-biotinyl-N'-methacryloyltrimethyleneamide. The UCST of the resulting magnetic fine particles was found to be 6° C.

Example 12

UCST magnetic fine particles were prepared in accordance with Example 2 with the exception that 132 mg of N-formylacrylamide was used instead of N-biotinyl-N'-methacryloyltrimethyleneamide. The UCST of the resulting magnetic fine particles was found to be 16° C.

Example 13

UCST magnetic fine particles were prepared in accordance with Example 2 with the exception that 221 mg of N-formylacrylamide was used instead of N-biotinyl-N'-methacryloyltrimethyleneamide. The UCST of the resulting magnetic fine particles was found to be 30° C.

Example 14

UCST magnetic fine particles were prepared in accordance with Example 2 with the exception that 237 mg of acrylamide was used instead of N-biotinyl-N'-methacryloyltrimethyleneamide. The UCST of the resulting magnetic fine particles was found to be 10° C.

Example 15

UCST magnetic fine particles were prepared in accordance with Example 2 with the exception that 188 mg of N-acetylacrylamide was used instead of N-biotinyl-N'-methacryloyltrimethyleneamide. The UCST of the resulting magnetic fine particles was found to be 12° C.

Example 16

UCST magnetic fine particles were prepared in accordance with Example 2 with the exception that 1.18 g of acrylamide and 275 mg of N-formylacrylamide were used instead of N-acryloylglycineamide and N-biotinyl-N'-methacryloyltrimethyleneamide. The UCST of the resulting magnetic fine particles was found to be 14° C.

While the invention has been described in detail and with reference to specific embodiments thereof, it will be apparent to one skilled in the art that various changes and modifications can be made therein without departing from the spirit and scope thereof.

This application is based on Japanese Patent Application No. 2000-249817 filed on Aug. 21, 2000 and the entire content thereof is incorporated herein by reference.

INDUSTRIAL APPLICABILITY

When the magnetic fine particles of the invention to which a polymer having an upper critical solution temperature is immobilized are used for separating a biological molecule or the like, it is possible to separate or recover the objective biological molecule or the like without damaging or inactivating it.

The invention claimed is:

1. Magnetic fine particles having immobilized thereto a polymer having an upper critical solution temperature,
wherein said polymer having an upper critical solution temperature is a polymer obtained by polymerizing at least a monomer represented by the following general formula (1):

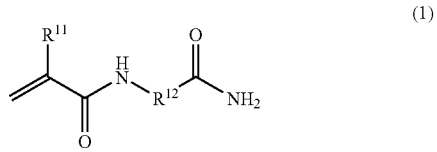

(1)

wherein $R^{11}$ represents a hydrogen atom or a methyl group and $R^{12}$ represents a single bond or a linear or branched alkylene group having 1 to 5 carbon atoms, and
at least a monomer represented by the following general formula (2):

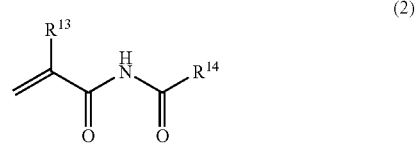

(2)

wherein $R^{13}$ represents a hydrogen atom or a methyl group and $R^{14}$ represents a hydrogen atom, a linear, branched, or cyclic alkyl group having 1 to 10 carbon atoms, an alkoxyl group, an alkylamino group, an aryl group, or a heterocyclic group.

2. Magnetic fine particles having immobilized thereto a polymer having an upper critical solution temperature,
wherein said polymer having an upper critical solution temperature is a polymer obtained by polymerizing at least a monomer represented by the following general formula (1):

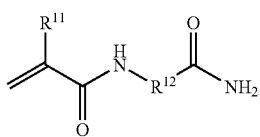

wherein $R^{11}$ represents a hydrogen atom or a methyl group and $R^{12}$ represents a single bond or a linear or branched alkylene group having 1 to 5 carbon atoms, and a monomer having biotin as part of its structure, wherein the monomer having biotin as part of its structure is a polymerizable biotin derivative represented by the following general formula (3):

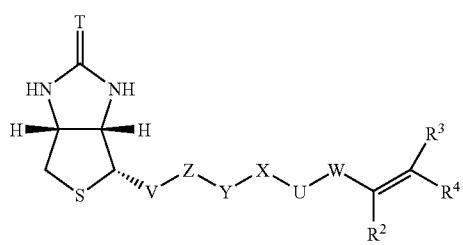

wherein $R^2$ represents a hydrogen atom or an alkyl group, $R^3$ and $R^4$ each independently represent a hydrogen atom, an alkyl group or an aryl group, T represents an oxygen atom or =NH group, W represents a single bond, a carbonyl group, a thiocarbonyl group, or an alkylene group having 1 to 5 carbon atoms, U represents a single bond or —NH— group, X represents a single bond, a hydrocarbon bond having 1 to 8 carbon atoms, an oxygen atom, or —NH— group, Y represents a single bond, a carbonyl group, a thiocarbonyl group, —NH— group, a 1,2-dioxyethylene group, or a 1,2-diaminoethylene group, Z represents a single bond, a carbonyl group, a thiocarbonyl group, an alkylene group having 1 to 5 carbon atoms, an oxygen atom, or —NH— group, and V represents a single bond or an alkylene group having 1 to 5 carbon atoms.

3. The magnetic fine particles according to claim 1, wherein said polymer having an upper critical solution temperature is a polymer obtained by polymerization additionally using at least one monomer selected from the group consisting of hydrophilic monomers and hydrophobic monomers.

4. The magnetic fine particles according to claim 1, wherein one of one pair of substances having a mutual specific action is immobilized to said polymer having an upper critical solution temperature.

5. The magnetic fine particles according to claim 4, wherein said one pair of substances having a mutual specific action is at least one combination selected from the group consisting of biotin and avidin, an antigen and an antibody, a polynucleotide and a polynucleotide having a complementary base sequence, a cDNA and an mRNA, an active site of an enzyme and a substrate, an active site of an enzyme and a product, an active site of an enzyme and a competitive inhibitor, a coenzyme binding site of an enzyme and a coenzyme, a coenzyme binding site of an enzyme and a triazine dye, a protease and a protease inhibitor, an Fc site and protein A, an Fc site and protein G, lectin and a sugar, a hormone receptor and a hormone, a DNA and a DNA binding protein, heparin and fibronectin, and heparin and laminin.

6. The magnetic fine particles according to claim 4, wherein said one pair of substances having a mutual specific action are biotin and avidin.

7. The magnetic fine particles according to claim 4, wherein one of said one pair of substances having a mutual specific action, immobilized to said polymer having an upper critical solution temperature is biotin.

8. The magnetic fine particles according to claim 7, wherein said biotin is a biotin bound to avidin (hereinafter referred to as "avidin-bound biotin").

9. The magnetic fine particles according to claim 7, wherein an avidinylated enzyme is bound to said biotin.

10. The magnetic fine particles according to claim 8, wherein a biotinylated enzyme is bound to said avidin-bound biotin.

11. The magnetic fine particles according to claim 7, wherein an avidinylated antibody is bound to said biotin.

12. The magnetic fine particles according to claim 8, wherein a biotinylated antibody is bound to said avidin-bound biotin.

13. The magnetic fine particles according to claim 7, wherein an avidinylated molecular chaperon is bound to said biotin.

14. The magnetic fine particles according to claim 8, wherein a biotinylated molecular chaperon is bound to said avidin-bound biotin.

15. The magnetic fine particles according to claim 7, wherein an avidinylated heat shock protein is bound to said biotin.

16. The magnetic fine particles according to claim 8, wherein a biotinylated heat shock protein is bound to said avidin-bound biotin.

17. The magnetic fine particles according to claim 7, wherein an avidinylated nucleic acid is bound to said biotin.

18. The magnetic fine particles according to claim 8, wherein a biotinylated nucleic acid is bound to said avidin-bound biotin.

19. The magnetic fine particles according to claim 2, wherein said polymer having an upper critical solution temperature is a polymer obtained by polymerization additionally using at least one monomer selected from the group consisting of hydrophilic monomers and hydrophobic monomers.

20. A separating agent containing said magnetic fine particles according to any one of claims 1, 8 or 19.

21. The magnetic fine particles according to claim 2, wherein the polymerizable biotin derivative represented by general formula (3) is further represented by one of the following general formulae (5) to (7):

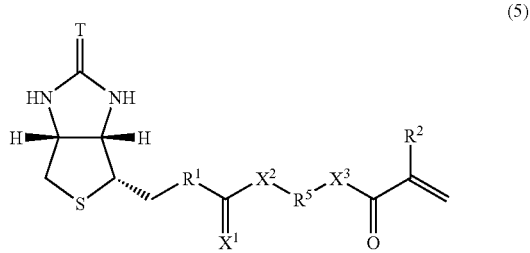

-continued (6)
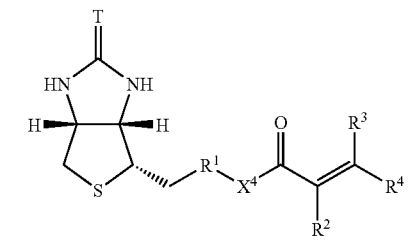

(7)
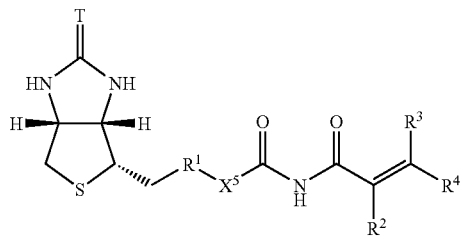

wherein $R^1$ represents a single bond or an alkylene group having 1 to 4 carbon atoms, $R^5$ represents an alkylene group having 2 or 3 carbon atoms, $X^1$ represents an oxygen atom or a sulfur atom, $X^2$ to $X^5$ each independently represent an oxygen atom or —NH— group, and T, $R^2$, $R^3$ and $R^4$ each has the same definition as in the above general formula (3).

22. The magnetic fine particles according to claim 2, wherein the polymerizable biotin derivative represented by general formula (3) is further represented by one of the following general formulae (13) to (15):

(13)
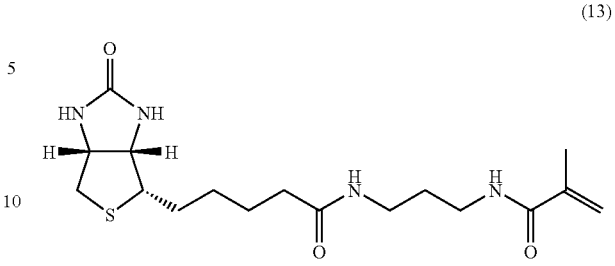

(14)
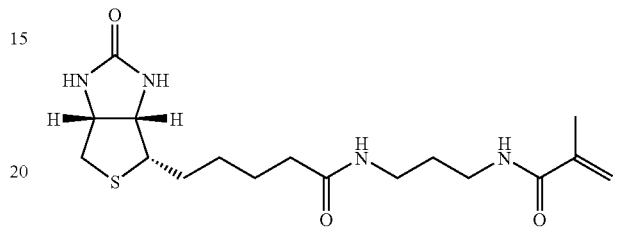

(15)
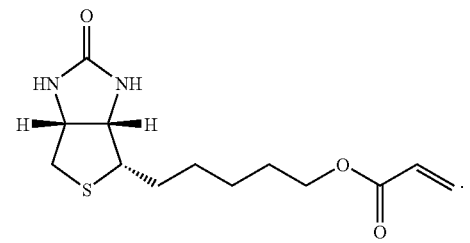

* * * * *